United States Patent
Beier et al.

(10) Patent No.: US 7,344,733 B2
(45) Date of Patent: Mar. 18, 2008

(54) MATRIX CONTROLLED TRANSDERMAL THERAPEUTIC SYSTEM FOR THE USE OF PRAMIPEXOLE AND ROPINIROLE

(75) Inventors: Cornelia Beier, Heidenheim (DE); Martina Wilhelm, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 627 days.

(21) Appl. No.: 10/484,876

(22) PCT Filed: Jul. 26, 2002

(86) PCT No.: PCT/EP02/08394

§ 371 (c)(1),
(2), (4) Date: Jul. 16, 2004

(87) PCT Pub. No.: WO03/015779

PCT Pub. Date: Feb. 27, 2003

(65) Prior Publication Data

US 2004/0247656 A1    Dec. 9, 2004

(30) Foreign Application Priority Data

Jul. 28, 2001   (DE) ................ 101 37 082

(51) Int. Cl.
*A61F 13/00*   (2006.01)
(52) U.S. Cl. ....................... 424/449; 424/448
(58) Field of Classification Search ............. 424/422, 424/448, 449
See application file for complete search history.

(56) References Cited

U.S. PATENT DOCUMENTS

| | | | |
|---|---|---|---|
| 5,399,355 A | 3/1995 | Riedl et al. | 424/448 |
| 5,462,744 A | 10/1995 | Gupte et al. | 424/448 |
| 5,738,869 A * | 4/1998 | Fischer et al. | 424/450 |
| 5,807,570 A | 9/1998 | Chen et al. | 424/449 |
| 6,221,383 B1 * | 4/2001 | Miranda et al. | 424/449 |

FOREIGN PATENT DOCUMENTS

| | | |
|---|---|---|
| AU | 199929341 B2 | 12/1999 |
| DE | 198 14 084 A1 | 10/1999 |
| EP | 1 027 889 A2 | 8/2000 |
| EP | 1 027 889 A3 | 8/2000 |

OTHER PUBLICATIONS

International Search Report in PCT/EP02/08394 dated Mar. 13, 2003.
International Preliminary Examination Report in PCT/EP02/08394 dated Dec. 1, 2003.
English-Language translation of International Preliminary Examination Report dated Feb. 17, 2004, in International Application No. PCT/EP02/08394.

* cited by examiner

*Primary Examiner*—Sharon E. Kennedy
(74) *Attorney, Agent, or Firm*—Marshall, Gerstein & Borun LLP

(57) ABSTRACT

The invention relates to an active-ingredient-containing, matrix-controlled transdermal therapeutic system for the use of pramipexole, ropinirole, pharmaceutically acceptable salts thereof or pharmaceutically acceptable derivatives thereof.

13 Claims, No Drawings

MATRIX CONTROLLED TRANSDERMAL THERAPEUTIC SYSTEM FOR THE USE OF PRAMIPEXOLE AND ROPINIROLE

This is the U.S. national phase of International Application No. PCT/EP02/08394 filed Jul. 26, 2002, the entire disclosure of which is incorporated herein by reference.

BACKGROUND OF THE DISCLOSURE

1. Field of the Disclosure

The invention relates to an active-ingredient-containing matrix-controlled transdermal therapeutic system for the use of pramipexole, ropinirole, pharmaceutically acceptable salts thereof or pharmaceutically acceptable derivatives thereof.

2. Brief Description of the Related Technology

Pramipexole and ropinirole are used for the treatment of Parkinson's disease. As a dopamine agonist, pramipexole [2-amino-6-n-propylamino-4,5,6,7-tetrahydrobenzo-thiazole] binds with high selectivity and specificity to the $D_2$ and $D_3$ receptors. Owing to its stimulating effect on the dopamine receptors in the corpus striatum, pramipexole produces a reduction in Parkinson's tremors. When administered orally, the daily dose is approximately from 1.5 to 4.5 mg with a bioavailability of 90%. However, the administration of even small amounts of pramipexole is associated with considerable side-effects in the patient. Ropinirole [4-(2-di-n-propylaminoethyl)-2-(3H)-indolone] acts as a dopamine agonist with high selectivity on the $D_2$ receptors. The daily dose is from 0.3 to 30 mg when administered orally. The bioavailability is 50%.

By means of a transdermal therapeutic system it is possible to circumvent the side-effects that occur in the case of oral administration of pramipexole or ropinirole. Transdermal administration furthermore has the advantage that the active ingredient, after permeation through the skin, has a direct systemic action, as a result of which a constant blood plasma level can be guaranteed. Hepatic metabolism of the active ingredient is also circumvented, that is to say, the burden on the liver is relieved. Gastrointestinal side-effects are avoided. The use of patches that retain their full effectiveness for several days, which in contrast to oral administration is simple and convenient, is an advantage for the patient. Since the system is applied externally, it can fulfil its intended function for a very long time without being changed.

There is already known from EP-B1-0 428 038 a transdermal system having a content of pramipexole and a) an active-ingredient-impermeable backing layer which is at the same time constructed as a covering plaster, b) an active-ingredient-containing reservoir (preferred carrier for the active ingredient is an emulsion-polymerised polyacrylate of the type Eudragit NE 30 $D^R$ produced by Röhm GmbH, Darmstadt) and c) a peel-off protective film (release liner).

Owing to surfactants or plasticisers and surface-active substances used in an emulsion-polymerised polyacrylate, a TTS produced according to EP-B1-0 428 038 does not exhibit sufficient stability of the active ingredient. In that matrix, pramipexole decomposes very rapidly, with discoloration occurring. In addition, the active ingredient crystallises out. That patch does not, therefore, have sufficient stability in storage.

WO 99/49853 proposes a moisture-activatable transdermal therapeutic system in which ropinirole hydrochloride is incorporated in a matrix together with an activator that gives a basic reaction in water, such as, for example, hydrated sodium silicate. The unstable ropinirole base, which has good permeation properties, is released from the stable ropinirole hydrochloride, which has a poor permeation capacity, only on the skin as a result of the admission of moisture. The release of the active ingredient and hence also the permeation of the active ingredient is therefore dependent on the moisture of the skin, which may possibly lead to irregular permeation rates and hence to fluctuating blood levels.

Matrix-TTSs having a content of ropinirole are described in WO 96/39136 and WO 97/11696.

In WO 96/39136, a TTS having a reservoir consisting of ropinirole base and lactose in a hydrogel (water, glycerine, polyvinyl alcohol, polyvinylpyrrolidone) is used.

WO 97/11696 describes a patch having a matrix consisting of ropinirole base, propylene glycol monolaurate and silicone adhesive.

Since ropinirole base is unstable, the above-mentioned systems would probably not be stable in storage for long.

DETAILED DESCRIPTION OF THE DISCLOSURE

The object of the present invention is to provide a matrix-TTS having a content of pramipexole, ropinirole, pharmaceutically acceptable salts thereof or pharmaceutically acceptable derivatives thereof, the stability of which with regard to the break-down of the active ingredient meets the standards required for authorisation. The active ingredient content is to be stable over a prolonged period and is to be subject to virtually no decomposition processes.

Surprisingly, it has now been found that a matrix-TTS comprising pramipexole, ropinirole, pharmaceutically acceptable salts thereof or pharmaceutically acceptable derivatives thereof as active ingredient is to a large extent stable towards decomposition if a self-adhesive matrix based on polyacrylates, especially solvent-containing polyacrylates, or on polyisobutylene is used.

The matrix patch consists of an impermeable cover layer, one or more self-adhesive matrix layer(s) containing the active ingredient and, where applicable, permeation enhancers/solubilisers, or one or more matrix layer(s) that are coated with a pressure-sensitive adhesive, and a peel-off protective layer. The active ingredient contained in the matrix is pramipexole, ropinirole, pharmaceutically acceptable salts thereof or pharmaceutically acceptable derivatives thereof.

Pharmaceutically acceptable salts of pramipexole, ropinirole or derivatives thereof are understood as being acid addition salts. The latter are obtained by reaction of the active ingredient in the form of the free base with pharmaceutically acceptable acids. Pharmaceutically acceptable acids are inorganic acids (for example hydrochloric acid, hydrobromic acid, sulfuric acid, nitric acid and phosphoric acid) or organic acids, especially carboxylic acids (for example acetic acid, propionic acid, hydroxyacetic acid, lactic acid, pyruvic acid, oxalic acid, maleic acid, malonic acid, succinic acid, fumaric acid, malic acid, tartaric acid, citric acid, methanesulfonic acid, ethanesulfonic acid, benzenesulfonic acid, p-toluenesulfonic acid, cyclohexanesulfamic acid, salicylic acid, p-aminosalicylic acid and pamoic acid). Solvates with the active ingredient are also referred to as acid addition salts. Such solvates are, for example, hydrates and alcoholates.

The amount of pramipexole, ropinirole, salts thereof or derivatives thereof used in the transdermal therapeutic system according to the invention ranges from 2 to 15% by weight of the weight of the matrix.

There come into consideration as the impermeable cover layer films that are acetal, acrylate, acrylonitrile-butadiene-styrene, acrylonitrile (methyl methacrylate) copolymer, acrylonitrile copolymer, ethylene ethyl acrylate, ethylene methyl acrylate, ethylene vinyl acetate, ethylene vinyl acetate copolymer, ethylene vinyl alcohol copolymer, ionomer, nylon (polyamide), nylon (polyamide) copolymer, polybutylene, polycarbonate, polyester, polyethylene terephthalate, thermoplastic polyester copolymer, polyethylene copolymer (high-density), polyethylene (high-molecular-weight, high-density), polyethylene (intermediate-molecular-weight, high-density), polyethylene (linear, low-density), polyethylene (low-density), polyethylene (medium-density), polyethylene oxide, polyimide, polypropylene, polypropylene (coated), polypropylene (oriented), polystyrene, polyurethane, polyvinyl acetate, polyvinyl chloride, polyvinylidene chloride and/or styrene-acrylonitrile filrris, which may, if required, be metallised or pigmented. Polyethylene terephthalate is preferred for the active-ingredient-impermeable cover layer.

For the pressure-sensitive adhesive layer, a pressure-sensitive adhesive, for example based on polyurethane, polyisobutylene, polyvinyl ether, polyacrylate or silicone or a mixture thereof, may be selected.

For the matrix, the matrix formers customary in medicine are used, such as polyacrylates, polyisobutylene, styrene/isoprene block copolymers or silicone adhesives. Preferably, a self-adhesive matrix that is based on solvent-containing polyacrylates and that, where applicable, is enhancer-resistant is used, it being possible for the matrix formers and the adhesives to be one and the same.

The matrix formers based on polyacrylates may be any desired homopolymer, copolymer or terpolymer consisting of various acrylic acid derivatives, where applicable with vinyl acetate.

For example, the polyacrylates may be polymers of one or more monomers of acrylic acid and other copolymerisable monomers. In addition, the polyacrylates may include copolymers of alkyl acrylates and/or alkyl methacrylates and/or copolymerisable secondary monomers or monomers having functional groups. If the amount of any type added as monomer is altered, the cohesive properties of the resulting acrylate polymers can be altered. In general, the acrylate polymer consists of at least 50% by weight of an acrylate, methacrylate, alkyl acrylate or alkyl methacrylate monomer, from 0 to 20% by weight of a functional monomer copolymerisable with acrylate, and from 0 to 50% by weight of another monomer.

Various acrylate monomers are mentioned hereinafter, such as, for example, acrylic acid, methacrylic acid, butyl acrylate, butyl methacrylate, hexyl acrylate, hexyl methacrylate, isooctyl acrylate, isooctyl methacrylate, glycidyl methacrylate, 2-hydroxyethyl acrylate, methyl acrylate, methyl methacrylate, 2-ethylhexyl acrylate and 2-ethylhexyl methacrylate, that may be polymerised individually or in admixture.

In addition, functional monomers that are copolymerisable with the above-mentioned acrylates, such as, for example, acrylic acid, methacrylic acid, hydroxyethyl acrylate, vinyl acetate, hydroxypropyl acrylate, acrylamide, dimethylacrylamide, acrylonitrile, dimethylaminoethyl acrylate, dimethylaminoethyl methacrylate, tert.-butylaminoethyl acrylate, tert.-butylaminoethyl methacrylate, methoxyethyl acrylate and methoxyethyl methacrylate, can be used for copolymerisation.

The content of adhesives in the self-adhesive matrix may be from 50 to 90% by weight, especially from 70 to 80% by weight, based on the weight of the matrix.

For the peel-off protective layer there come into consideration polyethylene terephthalate, polyester, polyethylene, polypropylene, polysiloxane, ethylene vinyl acetate, polyurethane or paper or a mixture thereof, usually with a silicone, fluorosilicone or fluorocarbon coating.

As permeation enhancers and/or solubilisers it is possible to use optionally saturated and/or unsaturated fatty alcohols each containing from 8 to 18 carbon atoms; tea tree oil; saturated and/or unsaturated cyclic ketones; alkyl methyl sulfoxides; saturated and/or unsaturated fatty acids each containing from 8 to 18 carbon atoms; esters and salts thereof; natural vitamin E (Copherol® F1300); synthetic vitamin E and/or vitamin E derivatives; sorbitan fatty acid esters and/or ethoxylated sorbitan fatty acid esters; azones (laurocapram); 1-alkylpyrrolidone; polyvinylpyrrolidone; block copolymers of polyethylene glycol and dimethylsiloxane with a cationic group at one end; polysiloxanes; polyoxyethylene-10-stearyl ether; mixture of polyoxyethylene-10-stearyl ether and glyceryl dilaurate; dodecyl-2-(N,N-dimethylamino)-propanol tetradecanoate and/or dodecyl-2-(N,N-dimethylamino)-propionate; N-acetylprolinate esters with >8 carbon atoms; non-ionic surfactants, for example lauryl ethers and/or esters of polyoxyethylene; dimethyl(arylimino)sulfuran; mixture of oleic acid analogues and propylene glycol; mixture of padimate 0, octyl salicylate, isopropyl myristate, isopropyl palmitate, octylmethoxy cinnamate and laurocapram or a mixture of individual components; phospholipids; highly dispersed silicon dioxide (Aerosil®); polyoxyethylene-7-glycerol monococoate (Cetiol® HE); 2-octyldodecanol (Eutanol® G) or a mixture of various individual components. Natural vitamin E (Copherol® F1300) is preferred as the permeation enhancer and/or solubiliser in the transdermal therapeutic system according to the invention.

The invention is described in more detail by the following Examples without, however, thereby limiting the scope of the invention.

EXAMPLE 1

Composition of a self-adhesive matrix according to the invention for a Pramipexole-TTS

| components | content in % by weight |
|---|---|
| pramipexole | 2.5 |
| Copherol ® F1300 | 7.5 |
| Durotak ® 387-2287 | 90.0 |

The percentages by weight relate to the weight of the matrix.

Production Process:

Pramipexole, isopropanol and ethyl acetate are weighed into a suitable stirring vessel and homogenised (active ingredient solution). In another suitable stirring vessel, Durotak® and Copherol® are weighed in, the active ingredient solution is added thereto and homogenisation is carried out. That mixture is applied to a film for the peel-off protective layer, for example transparent PET, and dried in a drying channel. A PET film (for example Hostaphan RN 19) for the active-ingredient-impermeable cover layer is then applied to that matrix. The patches are subsequently punched.

Determination of the Permeation of Pramipexole In Vitro Through Mouse Skin

Apparatus for the skin permeation:

| cells: | modified flow cell |
|---|---|
| skin: | hairless mouse from female mice |
| acceptor medium: | 0.9% sodium chloride + 0.05% sodium azide, 60 ml per cell |
| permeation temp.: | 32° C. ± 0.5° C. |

After taking samples, the active ingredient concentrations are then determined by means of HPLC.

| time [h] | permeation [mg/cm$^2$] |
|---|---|
| 24 | 0.17 |

Stability:

After a storage time of 12 months, the pramipexole-TTS with a matrix adhesive of Durotak® 387-2287 shows no discoloration or formation of crystals.

EXAMPLE 2

Composition of a Self-Adhesive Matrix According to the Invention for a Pramidexole-TTS

| components | content in % by weight |
|---|---|
| pramipexole | 3 |
| Copherol ® F1300 | 7.5 |
| Durotak ® 87-4287 | 89.5 |

The percentages by weight relate to the weight of the matrix.

Production Process:

Pramipexole, isopropanol and ethyl acetate are weighed into a suitable stirring vessel and homogenised (active ingredient solution). In another suitable stirring vessel, Durotak® and Copherol® are weighed in, the active ingredient solution is added thereto and homogenisation is carried out. The further processing is carried out analogously to Example 1.

Determination of the Permeation of Pramipexole In Vitro Through Mouse Skin

Apparatus for the skin permeation:

| cells: | modified flow cell |
|---|---|
| skin: | hairless mouse from female mice |
| acceptor medium: | 0.9% sodium chloride + 0.05% sodium azide, 60 ml per cell |
| permeation temp.: | 32° C. ± 0.5° C. |

After taking samples, the active ingredient concentrations are then determined by means of HPLC.

| time [h] | permeation [mg/cm$^2$] |
|---|---|
| 24 | 0.24 |

Stability:

After a storage time of 4 months, the pramipexole-TTS with a matrix adhesive of Durotakl 87-4287 shows no discoloration or formation of crystals.

EXAMPLE 3

Composition of a Self-Adhesive Matrix According to the Invention for a Pramipexole-TTS

| components | content in % by weight |
|---|---|
| pramipexole | 3 |
| Aerosil ® 200 | 2 |
| Copherol ® F1300 | 7.5 |
| Durotak ® 387-2287 | 87.5 |

The percentages by weight relate to the weight of the matrix.

Production Process:

Pramipexole, isopropanol and ethyl acetate are weighed into a suitable stirring vessel and homogenised (active ingredient solution). In another suitable stirring vessel, Durotak® Aerosil® and Copherol® are weighed in, the active ingredient solution is added thereto and homogenisation is carried out. The further processing is carried out analogously to Example 1.

Determination of the Permeation of Pramipexole In Vitro Through Mouse Skin

Apparatus for the Skin Permeation:

| cells: | modified flow cell |
|---|---|
| skin: | hairless mouse from female mice |
| acceptor medium: | 0.9% sodium chloride + 0.05% sodium azide, 60 ml per cell |
| permeation temp.: | 32° C. ± 0.5° C. |

After taking samples, the active ingredient concentrations are then determined by means of HPLC.

| time [h] | permeation [mg/cm$^2$] |
|---|---|
| 24 | 0.19 |

Stability:

After a storage time of 5 months, the pramipexole-TTS with a matrix adhesive of Durotak® 387-2287 with Aerosil® shows no discoloration or formation of crystals.

The invention claimed is:

1. A transdermal therapeutic system (TTS) for the administration of one or more active ingredients selected from the group consisting of pramipexole, pharmaceutically acceptable pramipexole salts, and pharmaceutically acceptable pramipexole derivatives, the system comprising:

(i) an active-ingredient-impermeable cover layer, (ii) a self-adhesive active-ingredient-containing matrix layer or a plurality of active-ingredient-containing matrix layers of which at least the matrix layer that is exposed upon application of the system is self-adhesive, and (iii) a peel-off protective layer, wherein the self-adhesive matrix layer comprises polyacrylate, a polyisobutylene, a styrene/isoprene block copolymer, or a silicone adhesive.

2. The system of claim 1, wherein the active ingredient comprises one or more salts pramipexole comprising reaction products of pramipexole or a pramipexole derivative and an acid.

3. The system of claim 1, wherein the active ingredient is one or more solvates comprising a reaction product of pramipexole, a pramipexole salt, or a pramipexole derivative and a solvate former.

4. The system of claim 1, wherein the active ingredient is a solvate salt of an inorganic or organic acid, and wherein the system is free of an acid-neutralizing base.

5. The system of claim 1, wherein the matrix layer is self-adhesive.

6. The system of claim 1, wherein the matrix layer comprises a polymer material free of plasticizers and/or surface-active substances of emulsion polymerization.

7. The system of claim 1, wherein the system is free of hydrogel.

8. The system of claim 1, wherein the one or more matrix layers comprises one or more members of the group consisting of permeation enhancers and solubilizers.

9. The system according to of claim 8, wherein the permeation enhancer and/or solubilizer is natural vitamin E.

10. The system of claim 2, wherein the acid is an inorganic acid selected from the group consisting of hydrochloric acid, hydrobromic acid, sulfuric acid, nitric acid, and phosphoric acid.

11. The system of claim 2, wherein the acid is an organic acid selected from the group consisting of acetic acid, propionic acid, hydroxyacetic acid, lactic acid, pyruvic acid, oxalic acid, maleic acid, malonic acid, succinic acid, fumaric acid, malic acid, tartaric acid, citric acid, methanesulfonic acid, ethanesulfonic acid, benzenesulfonic acid, p-toluenesulfonic acid, cyclohexanesulfamic acid, salicylic acid, p-aminosalicylic acid and pamoic acid.

12. The system of claim 3, wherein the solvate former is water or alcohol.

13. The system of claim 12, wherein the solvate former is an alcohol and the alcohol is ethyl alcohol.

* * * * *